United States Patent [19]
Matson

[11] Patent Number: 4,753,714
[45] Date of Patent: Jun. 28, 1988

[54] METHOD OF OPTIMIZING FLOW PATTERN AND INCREASING SIGNAL-TO-NOISE RATIOS IN ELECTROCHEMICAL FLOW THROUGH SENSORS

[75] Inventor: Wayne R. Matson, Ayer, Mass.
[73] Assignee: ESA, Inc., Bedford, Mass.
[21] Appl. No.: 85,324
[22] Filed: Aug. 10, 1987

Related U.S. Application Data

[63] Continuation of Ser. No. 797,616, Nov. 13, 1985, abandoned.

[51] Int. Cl.⁴ .............................................. B01D 27/26
[52] U.S. Cl. .................................. 204/1 T; 204/409; 204/412
[58] Field of Search .................... 204/1 T, 411, 182.8, 204/412, 409, 414; 436/151; 264/267, 516, 570

[56] References Cited

U.S. PATENT DOCUMENTS

1,736,293  11/1926  Van Denburg ...................... 264/570
2,962,768  12/1960  Scott .................................. 264/267

Primary Examiner—John F. Niebling
Assistant Examiner—Ben C. Hsing
Attorney, Agent, or Firm—Hayes, Davis & Soloway

[57] ABSTRACT

In electrochemical flow through sensors comprising at least one cell for the passage of a fluid for analysis therethrough, the method of optimizing the flow pattern and signal-to-noise ratio comprising the steps of loading the cell under high pressure with a first fluid which will set to a solid material; before the solid material solidifies, causing a second fluid immiscible with the first fluid to flow through the cell at low pressure to find the optimum flow path therethrough; and, with the immiscible fluid in the cell, allowing the first fluid to solidify. Bandspreading is improved because any offset, junctions, or potential traps that would induce drag or trapping effects on a test fluid flowing through the cell are reduced in size and/or number and/or eliminated. The signal-to-noise is improved as the result of filling spaces in the cell that may contribute to noise but do not contribute significantly to useful signal because of their location relative to the optimum flow path.

18 Claims, 3 Drawing Sheets

METHOD OF OPTIMIZING FLOW PATTERN AND INCREASING SIGNAL-TO-NOISE RATIOS IN ELECTROCHEMICAL FLOW THROUGH SENSORS

This is a continuation of co-pending application Ser. No. 797,616 filed on Nov. 13, 1985, now abandoned.

BACKGROUND OF THE INVENTION

The present invention relates to electrochemical sensors and, more particularly, to methods for improving bandspreading and improving the signal-to-noise ratio in electrochemical flow through sensors. The invention has particular utility with electrochemical sensors of the coulometric type and will be described in such utility.

Electrochemical flow through sensors are well established in the art as useful analytical tools, particularly for, although not limited to, detection and determination of trace impurities in water, or the detection and determination of trace compounds in biological samples or the like. Recently, flow sensors of essentially 100% efficiency or coulometric type (as opposed to amperometric sensors with an efficiency of 3-5%) as typified by U.S. Pat. Nos. 4,404,065; 4,233,031; 4,413,505; 4,497,199 and 4,511,659 (all of which are assigned to the common assignee of this application) incorporating a series of porous conductive detector or working electrodes have been shown to have several unique applications in industrial and biomedic problems.

Figure 1:
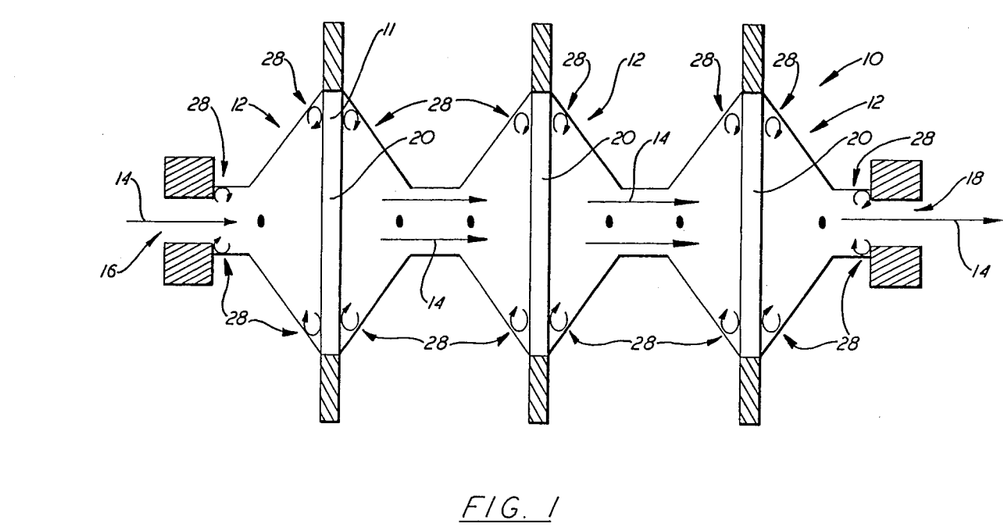
FIG. 1 is a simplified cutaway elevation drawing of a multi-cell sensor as wherein the present invention is applicable.
Figure 2:
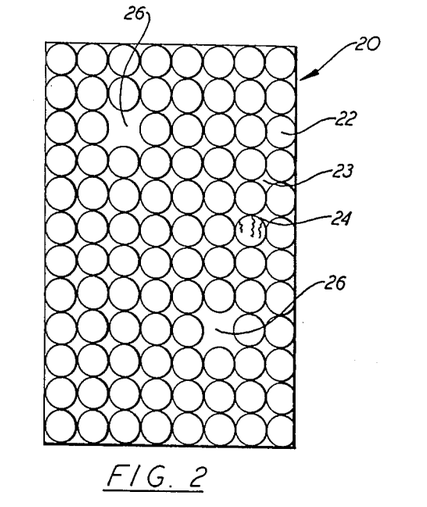
FIG. 2 is an enlarged simplified drawing of a portion of one of the detector electrodes of the sensor of FIG. 1 in the area designated as II.

A typical sensor of this type is shown in simplified form in FIG. 1. The sensor, generally indicated at 10, comprises a series of cells, generally indicated as 12, which define a path for the flow of test fluid 14 therethrough between the inlet at 16 and the outlet at 18. While a single cell 12 can be used, it is common to place a number of cells 12 in series to develop a larger electrical signal to more accurately reflect the characteristics of the test fluid 14. Each cell 12 typically contains a porous detector electrode 20 across the path of flow of the test fluid 14 through the cell 12. It is the detector electrode 20 in each cell 12 which develops the electrical signal of interest as the test fluid 14 passes through it. As shown in the enlarged drawing of FIG. 2, the detector electrode 20 is comprised of a porous electrode base material 22 such as fritted graphite or fritted carbon with pores 23. The porous material 22, in turn contains intersticial spaces 24 in the underlying matrix of the porous material 22. Since it is virtually impossible to create a homogeneous fritt material wherein the intersticial spaces 24 are completely uniform throughout, the porous material 22 also may contain enlarged secondary pores 26. Characteristically, the fluid 14 will find an optimum path through the cells 12 of the sensor 10. These enlarged secondary pores 26 and interstitial spaces 24 can be a source of noise, particularly when they are out of the optimum path and, therefore, not contributing in any substantial manner to the signal of interest being developed.

Also, junctions and traps in the construction of the sensor 10, such as those generally indicated at 28, can reduce the bandspreading of the cells 12 by inducing drag and trapping effects on the test fluid 14.

Wherefore, it is the object of the present invention to overcome the aforesaid and other disadvantages of the prior art and to provide a method of improving the bandspreading and reducing the signal-to-noise ratio in such sensors by vitually eliminating the effects of junctions, traps and secondary pores in the construction.

SUMMARY OF THE INVENTION

The foregoing objects have been achieved in electrochemical flow through sensors comprising at least one flow cell for the passage of a test fluid therethrough for analysis by the steps of loading the cell under high pressure with a fluid which will set to a solid material; before the material solidifies, flowing an immiscible fluid through the cell at low pressure to define the optimum path therethrough; and, with the immiscible fluid still in the cell, allowing the material to solidify.

In the preferred embodiment of the invention, the setting fluid is a meltable polymer loaded at or above its melt temperature which will cool to a solid; and the method additionally comprises the step of, with the immiscible fluid in the cell, cooling the cell to solidify the melted polymer. The cell may then be used directly. Alternatively and preferably the cell is then rinsed with a fluid that etches the surface of the polymer deposited along the optimum path to expose any residual polymer covering the active surface of the detector in the optimum path.

DESCRIPTION OF THE DRAWINGS

For a fuller understanding of the nature and objects of the present invention, reference should be had to the following detailed description taken in combination with the accompanying drawings, wherein.

DESCRIPTION OF THE PREFERRED EMBODIMENT

Figure 3:
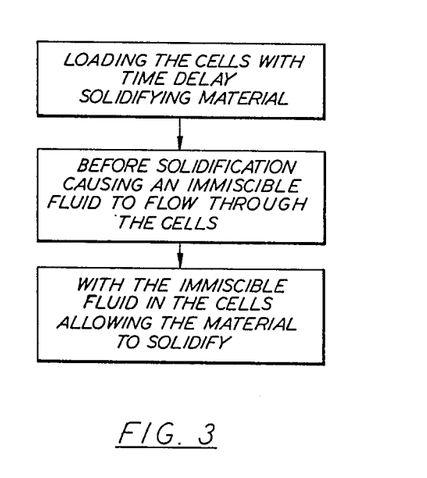
FIG. 3 is a block diagram setting forth the basic steps of the method of the present invention in general fashion.

The basic premise of the present invention is set forth in the block diagram of FIG. 3. The cells 12 are first loaded with a first fluid material which is "settable" to a solid, and a second fluid immiscible with the first fluid then is passed through the cells. The second fluid "finds" or defines the optimum flow path through the cells, and sweeps the first fluid from this path. The first fluid then is solidified resulting in a sensor with the optimum flow path exposed to test fluid passing therethrough and the irregularities which contribute to the problems described above masked from interference by the solidified material.

The settable fluid can be a material of the type that will turn to a solid after a time delay such as an epoxy, phenol-formaldehyde or styrene monomer. Alternatively, the setting fluid can be a meltable material loaded at or above its melt temperature which upon cooling will form a solid such as a naturally occurring or synthetic wax, or a meltable polymeric material such as polyethylene or polypropylene. The setting fluid also may be a thermal setting polymer, many of which are commercially available. The specific examples set forth herein will be with respect to the use of meltable polymeric materials.

Figure 4:
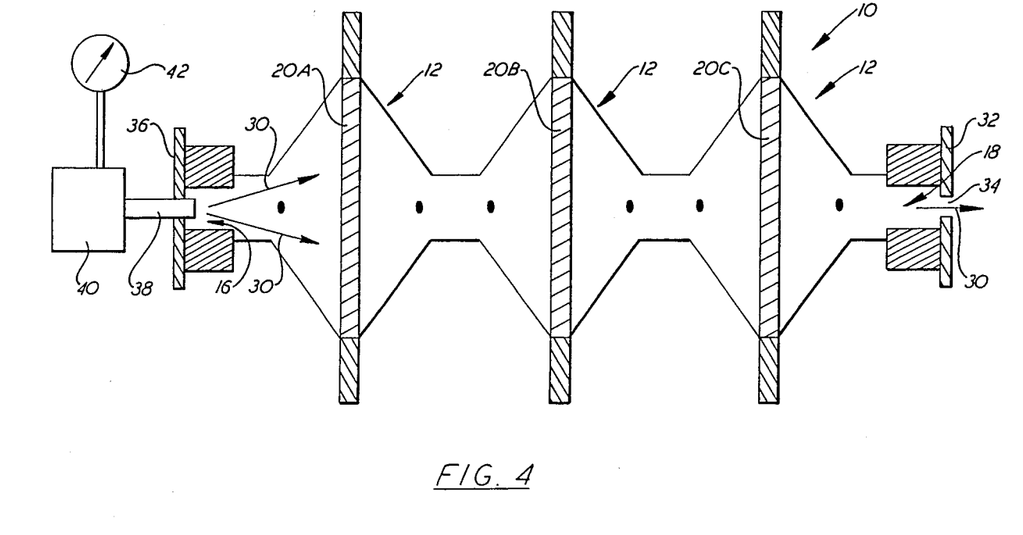
FIG. 4 shows the sensor of FIG. 1 during the step of the present invention in its preferred embodiment wherein the fluid polymeric material is pumped through the cells under high pressure.
Figure 5:
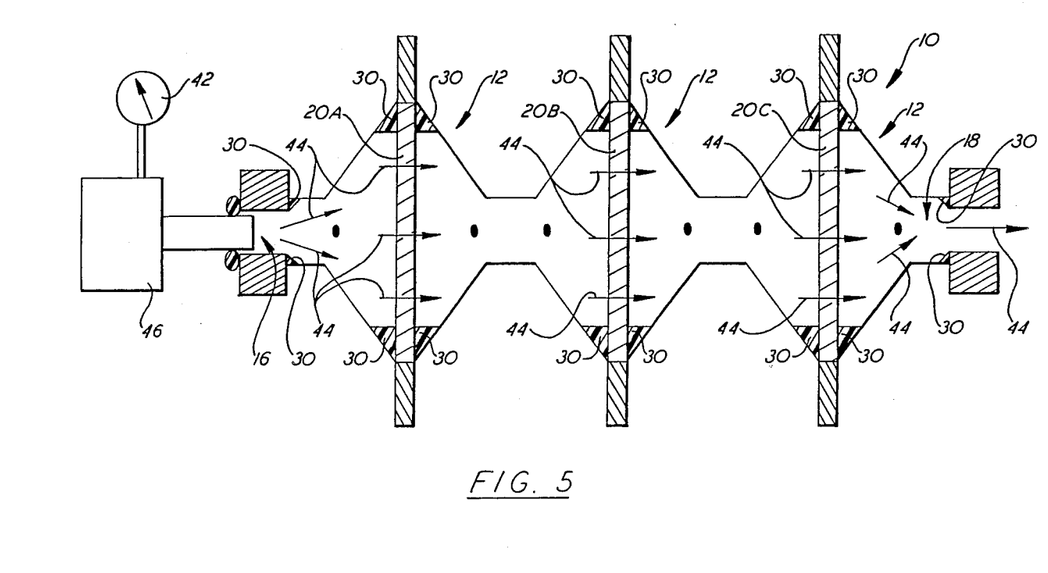
FIG. 5 shows the sensor of FIG. 1 during the step of the present invention in its preferred embodiment wherein the immiscible fluid is pumped through the cells and the fluid polymeric material contained therein to define the optimum flow path therethrough.
Figure 6:
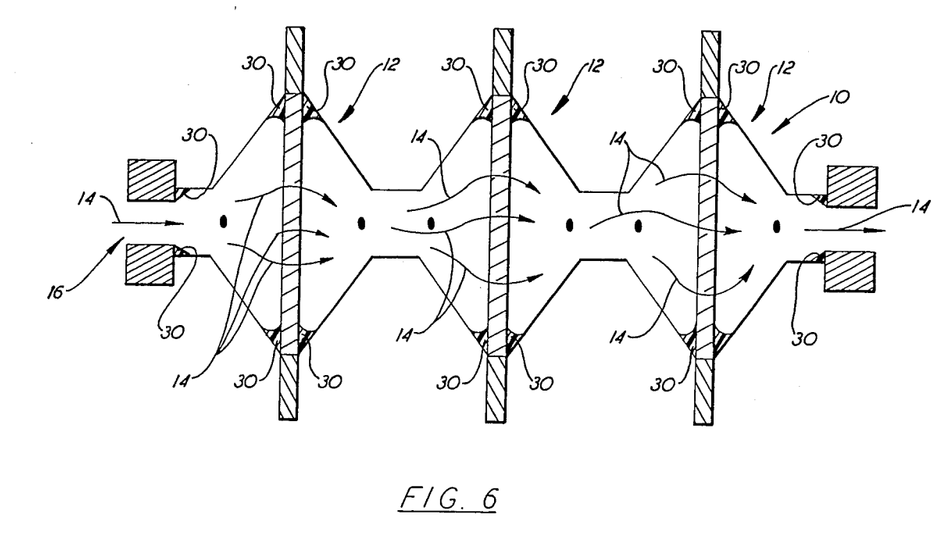
FIG. 6 shows the sensor of FIG. 1 with test fluid flowing therethrough after flow path optimization by the method of the present invention.
Figure 7:
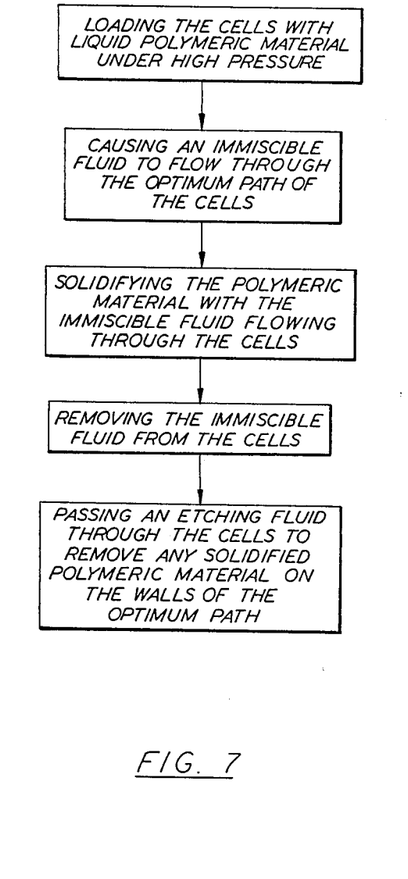
FIG. 7 is a block diagram setting forth in more detail the steps of the method of the present invention in its preferred embodiment.

The preferred embodiment of the present invention is set forth in block diagram form in FIG. 7 and the various steps thereof are shown in FIGS. 4–6.

As shown in FIG. 4, a melted polymeric material 30 is forced through the cells 12 under high pressure. This can be accomplished by closing down the outlet 18 with a plate 32 having a reduced orifice opening 34 therethrough. The inlet 16 is likewise closed down with a plate 36 having a nozzle 38 therethrough connected to a source 40 of the melted polymeric material 30 under a high pressure as indicated by the pressure gauge 42. By forcing the polymeric material 30 through the cells 12 under high pressure, the material 30 is forced into all the junction and trap areas 28 as well as into the secondary inherent pores 26 of the porous electrodes 20A, 20B, 20C.

Turning next to FIG. 5, a fluid 44 immiscible with the melted polymeric material 30 is next pumped from source 46 through the cells 12 and porous electrodes 20A, 20B, 20C. Ideally the flow volume is adjusted to substantially equal or slightly exceed that intended for the flow of test fluid through the sensor 10 under actual use. This step results in the fluid 44 seeking out and defining the optimum path for flow through the sensor 10. The fluid 44 passing through the sensor 10, being immiscible with the melted polymeric material 30 flushes the fluid polymeric material 30 along the optimum path from the sensor 10 while leaving the polymeric material 30 in the remaining areas essentially undisturbed.

It is preferred that the flow of the immiscible fluid 44 be maintained while the polymeric material 30 is allowed to solidify. Alternatively, the fluid 44 can be maintained statically within the sensor 10, cells 12, and detectors 20, e.g. as by closing off the inlet 16 and outlet 18 while solidification takes place.

Following solidification of the polymeric material 30, the cell may then be flushed and put into service. It is preferred, however, that subsequent to the solidification of the polymeric material 30, to flush the sensor 10 with an etching fluid which will remove any residual polymeric material 30 along the walls of the optimum path which was not flushed out by the passage of the immiscible fluid 44. This step simply assures that the maximum active surface of the porous detector electrodes in the optimum path will be available to generate the signal as a result of the test fluid 14 passing therethrough.

The result of the foregoing process leaves the sensor 10 as shown in use in FIG. 6. The solidified polymeric material 30 remains in the areas off of the optimum path to eliminate the problems previously associated therewith while the test fluid 14 is free to flow unhampered along the optimum path. More specifically, the process accomplishes several things:

1. Loading the cell with a liquid setting fluid at relatively high pressures causes the fluid to be forced into any void in the sensor including:
   (a) those left in the manufacturing process;
   (b) secondary or inherent pores in the porous electrode material;
2. When the cell is flushed with an immiscible fluid at low pressure, the flushing fluid seeks the optimum flow path, leaving the liquid setting fluid in any manufacturing voids or corners and the secondary inherent pores in the sensor material impregnated with the setting fluid;
3. Leaving the immiscible fluid in or flowing through the cell while the setting fluid is set maintains the optimized flow path as the setting fluid solidifies; and
4. Etching the cell by flowing through it, a fluid which attacks the solidified setting fluid preferentially etches any remaining polymer from the sensor surfaces in the optimum path. Thus any film or residue remaining on the sensor that otherwise might affect its performance can be removed without substantially attacking either the material filling the secondary porosity or manufacturing voids.

The specifics of tested embodiment and the results achieved thereby will now be described in detail.

EXAMPLE

The sensor treated was a multiple electrode flow cell as described in FIG. 1 of my prior U.S. Pat. No. 4,511,659.

In the first step, a melted polymer mixture comprising 67 volume percent $C_{48}$ hydrocarbon and 33 volume percent 0.916 density polyethylene, heated to 98° C. was pumped into the cell at 800 psi. Thereafter, water heated to 98° C. was passed through the cell at 0.1 mL/min at 20 psi. The cell was then cooled from 98° C. to ambient (25° C.) over a 15 minute time period by continuing the flow of cooler and cooler water.

Thereafter, the cell was flushed at 1 ml/min for 30 minutes with 10/10/80 THF hexane acetonitrile.

Disassembly of the cell following testing showed the retention of the solidified polymeric material at various locations 30. From performance testing of the cell polymeric material retention also was inferred at various intersticial spaces in the underlying matrix of the porous electrodes.

The before and after treatment performance characteristics of the flow cell are shown below:

|  | BEFORE | AFTER |
| --- | --- | --- |
| Efficiency of the first in line electrode 20A to hydroquinone | 99.7% | 99.7% |
| Efficiency of second in line electrode 20B to hydroquinone | 99.3% | 99.4% |
| Bandspreading electrode 20A (μl at 13.7% peak height) | 37.3 | 17.8 |
| Bandspreading electrode 20B (μl at 13.7% peak height) | 38.1 | 18.3 |
| Signal at electrode 20B to 10 pg Norepinephrine, Condition 1 | 1.8 na | 1.8 na |
| Noise at electrode 20B Condition 1 | 0.7 na | 0.2 na |
| Background Current at electrode 20B | −11 na | −12 na |
| Signal at electrode 20B to 100 pg histamine, Condition 2 | 7.2 na | 7.4 na |
| Noise at electrode 20B, Condition 2 | 3.2 na | 0.4 na |
| Background Current at | 16 μa | 0.8 μa |

|         | BEFORE | AFTER |
|---------|--------|-------|
| electrode 20B | | |

Condition 1.
Detector: electrode 20A at +400 mV
electrode 20B at −260 mV
Column: Brownlee 100 × 4.6 mm RP18 ODGU 5μ
Pump: ESA 5700
Mobile Phase: 5% CH₃CN, 100 mg/L octane sulfonic acid, 0.1 F NaH₂PO₄ adjusted to pH 2.3 with H₃PO₄
Flow Rate: 1.5 mL/min Condition 2.
Detector: electrode 20A at +650 mV
electrode 20B at +980 mV
Column, pump and flow rate as in Condition 1.
Mobile phase: 35% MeOH, 100 mg/L SDS (sodium dodecyl sulfonic acid) 0.1 F NaH₂PO₄ adjusted to pH 4.0 with H₃PO₄

The above-described improvements in the operating characteristics of the sensors are believed to result from the effect of the treatment on several sensor phenomena.

1. Bandspreading is improved in part because any offset, junctions or potential traps that would induce drag or trapping effect essentially have been eliminated.
2. The signal-to-noise improvement results from filling spaces in the porous electrode substrate material thereby eliminating regions within the electrode that contribute to noise but, since they are not in efficient regions of the flow path, do not contribute to signal. This area reduction (A) limits three types of noise:
   (a) Current changes ($\Delta i$) resulting from voltage fluctuations ($\Delta E$) acting on the double layer capacitance of the electrode ($C_{dl}$), following $\Delta i = E \times C_{dl}$ where $C_{dl} = kA$;
   (b) Currents resulting from changes in concentration of compounds with non-diffusion limited reactions in the flowing stream, e.g. column bleed or mobile phase reaction;
   (c) Currents resulting from pressure fluctuations causing a penetration of the sensor with the mobile phase, a change in the area ($\Delta A$) and hence the double layer capacity following following $\Delta i = VC_{dl}$ where $C_{dl} = kA$.

Filling the intermatrix micropores of the porous electrode substrate material in the flow region that is still active reduces noise by junction irregularities under condition 1.

Under the second operating condition, the noise and background current reduction results again from blocking the unused portions of the porous electrode substrate material and filling the secondary matrix pores. The noise reduction, more substantial than in the first operating condition, is believed to result from a different mechanism. More particularly, under the second operating condition, currents in the anodic potential region are observed primarily from the beginning of the wave of oxidation of the carrier mobile phase itself and are virtually completely potential limited rather than diffusion limited. Thus, when the spaces and pores are not filled, they may be penetrated to a greater or lesser extent by the mobile phase. Accordingly, the total area of the sensor including non-flow regions and pores is the area available for background signal noise. Noise can then be caused by changes in the area by pressure variation or potential fluctuations, which each linearly affect the observed currents. Filling or masking these regions presents a substantially lower area for potential limited mobile phase reactions while not impacting significantly the area for diffusion limited reactions that constitute the analytical signal.

The invention is susceptible to modification. For example, a liquid monomer may be loaded into the cell under pressure. Thereafter, an immiscible liquid containing a polymerization activator may be flowed through the cell under low pressure to achieve the dual purposes of defining the optimal flow path and effecting polymerization of the monomer to a solid. Still other changes and advantages will be obvious to one skilled in the art.

Wherefore, having thus described my invention, I claim:

1. In electrochemical flow through sensors comprising at least one cell for the passage of a fluid for analysis therethrough at predetermined rate, said cell including at least one porous electrode through which the fluid to be analyzed is passed, said porous electrode having interstitial and secondary pores, the method of optimizing the flow pattern and signal-to-noise ratio comprising the steps of:
   (a) loading the cell under a first pressure with a first fluid which is settable to a solid material so as to impregnate substantially all interstitial and secondary pores in said porous electrode;
   (b) before the solid material solidifies, flowing a second fluid immiscible with the first fluid through the cell at a second pressure, lower than the first pressure, to define a flow path therethrough at a flow rate similar to the predetermined rate; and
   (c) with the immiscible fluid still in the cell, solidifying the first fluid within the interstitial and secondary pores outside of said flow path.

2. The method of claim 1 wherein:
the immiscible fluid is maintained statically within the cell while the settable fluid solidifies.

3. The method of claim 1 wherein:
the immiscible fluid is maintained in a flowing condition through the cell while the settable fluid solidifies.

4. The method of claim 1 wherein:
the settable fluid is loaded into the cell under a pressure of between 600 and 1600 psi.

5. The method of claim 1 wherein:
the settable fluid is a material that will turn to a solid after a time delay.

6. The method of claim 5 wherein:
the settable fluid is a material selected from the group consisting of an epoxy, a phenol-formaldehyde and a styrene monomer.

7. The method of claim 1 wherein:
(a) the settable fluid is a meltable material loaded at or above its melt temperature; and,
(b) the step of causing an immiscible fluid to flow through the cell includes the step of maintaining the setting fluid at or above its melt temperature for a time.

8. The method of claim 7 wherein:
the settable fluid is selected from the group consisting of paraffin, polyethylene, polypropylene, and mixtures thereof.

9. The method of claim 1 wherein:

(a) the settable fluid is a meltable polymer loaded at or above its melt temperature; and additionally comprising the steps of, (b) with the immiscible fluid in the cell, cooling the cell to solidify the melted polymer.

10. The method of claim 9 and additionally comprising the step of:

rinsing the cell with a fluid that etches the surface of the solidified polymer whereby some solidified polymer along the walls of the flow path is removed.

11. The method of claim 1 wherein:

(a) the settable fluid is a thermal setting polymer; and (b) with the immiscible fluid in the cell the step of heating said polymer to cause it to solidify.

12. In electrochemical flow through sensors comprising at least one cell for the passage of a fluid for analysis therethrough, said cell including at least one porous electrode through which fluid to be analyzed is passed, said porous electrode having interstitial and secondary pores, the method of optimizing the flow pattern and signal-to-noise ratio comprising the steps of:

(a) loading the cell with a liquid mixture of a hydrocarbon and polyethylene at or about its melting point and about 800 psi so as to impregnate substantially all interstitial and secondary pores in said porous electrode;

(b) causing an immiscible fluid comprising water at about the melting point of the liquid mixture to flow through the cell at about 0.1 ml/min and about 20 psi to find a flow path therethrough, leave the liquid mixture in any manufacturing voids or corners, and leave in secondary pores in the porous electrode of the cell, located outside of said flow path, impregnated with the mixture; and (c) with the immiscible fluid in the cell, solidifying the mixture by cooling the cell to below the melting point of the liquid mixture.

13. In electrochemical flow through sensors comprising at least one cell for the passage of a fluid for analysis therethrough, said cell including at least one porous electrode through which the fluid to be analyzed is passed, said porous electrode having interstitial and secondary pores, the method of optimizing the flow pattern and signal-to-noise ratio comprising the steps of:

(a) loading the cell at a first pressure with a polymeric material at or above its melt temperature so as to impregnate substantially all interstitial and secondary pores in said porous electrode;

(b) causing a fluid immiscible with the melted polymeric material at a temperature substantially equal to that of the melted polymeric material to flow through the cell to define a flow path therethrough, leaving the polymeric material in any manufacturing voids or corners, and leaving in secondary pores in the porous electrode of the cell, located outside of said flow path, impregnated with the polymeric material; and (c) with the immiscible fluid in the cell, solidifying the polymeric material by cooling the cell to below the melting point of the polymeric material.

14. The method of claim 12 and additionally comprising the step of:

flushing the cell with a fluid capable of etching the solidified polymeric material to remove any film or residue of the polymeric material from the sensors along the flow path.

15. The method of claim 14 wherein the flushing step comprises:

flushing the cell at about 1 mL/min. with 10/10/80 THF hexane acetonitrile.

16. The method of claim 12 wherein:

(a) the mixture comprises a mixture of a hydrocarbon and polyethylene at or above its melting point and about 800 psi;

(b) the immiscible fluid comprises water at or above the melting point of the mixture flowing through the cell at about 0.1 mL/min. and about 20 psi; and, (c) the cooling step comprises cooling the cell to below the melting point of the mixture.

17. In a flow through sensor comprising at least one cell for the passage of a fluid for analysis therethrough and having a porous detector material therein, said cell including at least one porous electrode through which the fluid to be analyzed is passed, said porous electrode having interstitial and seconary pores, the method of optimizing the flow pattern and signal-to-noise ratio comprising the steps of:

(a) loading the cell with a fluid settable to a solid material at a first pressure high enough to force the fluid into any voids and irregularities in the cell and detector material;

(b) before the solid material solidifies, causing a fluid immiscible with the settable fluid to flow through the cell at a second pressure, lower than the first pressure, to define a flow path therethrough and clear the settable fluid from the path; and (c) with the immiscible fluid in the cell, solidifying the settable fluid within all interstitial and secondary pores outside of said flow path.

18. The method of claim 17 and additionally comprising the step of:

rinsing the cell with a fluid that etches the surface of the solidified settable fluid whereby some solidified settable fluid along the walls of the flow path is removed.

* * * * *